United States Patent [19]

Kolb

[11] Patent Number: 5,415,643

[45] Date of Patent: May 16, 1995

[54] FLUSHABLE ABSORBENT COMPOSITES

[75] Inventor: Thomas M. Kolb, Neenah, Wis.

[73] Assignee: Kimberly-Clark Corporation, Neenah, Wis.

[21] Appl. No.: 987,049

[22] Filed: Dec. 7, 1992

[51] Int. Cl.⁶ ............................................. A61F 13/15
[52] U.S. Cl. ................................. 604/367; 604/368; 604/370
[58] Field of Search ............ 604/358, 367, 368, 385.1, 604/370

[56] References Cited

U.S. PATENT DOCUMENTS

| | | | |
|---|---|---|---|
| Re. 32,649 | 4/1988 | Brandt et al. | |
| 4,025,472 | 5/1977 | Lepoutre | 260/17.4 GC |
| 4,043,952 | 8/1977 | Ganslaw et al. | 260/17.4 ST |
| 4,090,013 | 5/1978 | Ganslaw et al. | 526/15 |
| 4,127,944 | 12/1978 | Giacobello | 34/9 |
| 4,548,847 | 10/1985 | Aberson et al. | 428/74 |
| 4,654,039 | 3/1987 | Brandt et al. | 604/368 |
| 4,666,975 | 5/1987 | Yamasaki et al. | 524/733 |
| 4,693,713 | 9/1987 | Chmelir et al. | 604/368 |
| 4,952,550 | 8/1990 | Wallach et al. | 604/368 |
| 5,026,363 | 6/1991 | Pratt | 604/385.1 |
| 5,061,259 | 10/1991 | Goldman et al. | 604/368 |
| 5,141,794 | 8/1992 | Arroyo | 604/370 |
| 5,147,343 | 9/1992 | Kellenberger | 604/368 |
| 5,176,668 | 1/1993 | Bernardin | 604/368 |
| 5,180,622 | 1/1993 | Berg et al. | 604/368 |
| 5,195,999 | 3/1993 | Harada et al. | 604/368 |
| 5,206,205 | 4/1993 | Tsai | 604/368 |

Primary Examiner—Randall L. Green
Assistant Examiner—Rob Clarke
Attorney, Agent, or Firm—Gregory E. Croft

[57] ABSTRACT

Absorbent composite structures containing fluff pulp and a superabsorbent material, such as those useful for disposable diapers, can be made to be flushable if the superabsorbent has the requisite properties. It has been found that flushability of such composite structures is enhanced when using superabsorbent materials having a ratio of the Absorbency Under Load (AUL) to the Centrifuge Retention Capacity (CRC) of about 0.70 or greater.

22 Claims, 1 Drawing Sheet

FLUSHABLE ABSORBENT COMPOSITES

BACKGROUND OF THE INVENTION

Disposable diapers have gained widespread acceptance by consumers because of their convenience and performance. However, a source of inconvenience has been disposal of the soiled diapers. Most households have municipal garbage pick-up about once a week and soiled diapers consequently accumulate in the garbage for several days, sometimes causing an undesirable odor. In addition, there has been some concern expressed regarding the contribution of disposable diapers to the growing shortage of landfill space.

One possible solution to these concerns would be a flushable diaper. It is currently possible to provide a disposable diaper with a removable absorbent pad which, when soiled, can be flushed down the toilet. Such a product design can eliminate the odor problem associated with accumulating soiled diapers and also lessens the burden on landfill waste sites. An example of such a diaper is described in commonly assigned copending application Ser. No. 07/816,457 entitled "Disposable Absorbent Article With Flushable Insert" and filed Dec. 31, 1991 in the names of T. H. Roessler, A. Cesco-Cancion, D. Endres, and P. M. Hanson, which is herein incorporated by reference. Other examples of diapers with flushable portions include U.S. Pat. No. 3,667,466 to H. J. Ralph and U.S. Pat. No. 4,964,857 to C. Osborn. In general, diapers with flushable inserts have the same basic components as regular disposable diapers including, without limitation, a liquid impervious backsheet, a liquid pervious bodyside liner, and an absorbent composite material, which can be in the form of a removable absorbent pad, disposed between the bodyside liner and the backsheet. The manner in which the absorbent pad is attached to or removed from the diaper may vary.

However, flushing an absorbent pad can cause difficulties due to the large mass of superabsorbent and fibers necessary for proper performance of the absorbent pad. Therefore, there is a need for an absorbent composite which reduces the risk of plugging a toilet when flushed down the drain.

SUMMARY OF THE INVENTION

It has now been discovered that the flushability of an absorbent composite comprising a matrix of fluff pulp fibers and gelled superabsorbent particles can be improved by increasing the stiffness of the gelled superabsorbent. Surprisingly, the fibrous network of fluff fibers rather than the superabsorbent has been found to be the major factor in causing toilet plugging. The superabsorbent gel, although substantially greater in mass, apparently does not have the integrity and hence plugging propensity as does the fibrous network. When flushed, a typical superabsorbent gel will flex and "go with the flow", thus retaining the integrity of the gel/fluff structure. Contrary to expectations, however, it has been discovered that a stiffer gel structure, rather than creating a less flushable object, instead provides the superabsorbent gel a degree of brittleness, yet with enough integrity to break up during flushing and at the same time break up the fiber network with it. Stiffening the gel structure can be achieved by increasing the surface crosslinking of the superabsorbent particles. This property, however obtained, is manifested by the ratio of the Absorbency Under Load (AUL) (hereinafter defined) divided by the Centrifuge Retention Capacity (CRC) (hereinafter defined).

In addition, the swelling rate of the superabsorbent gel (as defined by the 30 Second Absorbent Capacity, hereinafter defined) has also been found to be a contributing factor in determining the flushability of a superabsorbent/fiber composite. As the absorbent structure comes in contact with the toilet bowl water the superabsorbent gel imbibes fluid, resulting in two detrimental effects on flushability. First, the superabsorbent swells, which creates extra absorbent volume which must pass through the narrow toilet trapway. Second, the amount of bowl water available for transporting material out of the toilet is reduced, thus reducing flushing efficiency. To limit these effects, it is desireable to have a superabsorbent gel which exhibits minimal swelling during the 5 to 30 seconds that typically elapses between placement of the absorbent structure into the toilet and flushing.

Accordingly, the invention resides in a flushable absorbent composite comprising a matrix of fluff pulp fibers and superabsorbent particles wherein the superabsorbent particles have an AUL:CRC ratio of about 0.70 or greater, preferably about 0.90 or greater, and more preferably about 1.10 or greater. Preferably the superabsorbent gel also has a 30 Second Absorbent Capacity (hereinafter described) of about 12 or less, more preferably about 6 or less. It is also preferred that the absorbent composite have about 50 weight percent or greater superabsorbent particles, preferably about 70 percent or greater, and more preferably about 80 percent or greater, based on the combined dry weight of the superabsorbent particles and the pulp fibers.

In another aspect, the invention resides in a disposable diaper comprising a liquid impervious backsheet, a removable absorbent pad containing an absorbent composite, and a liquid permeable bodyside liner, wherein the absorbent composite is as described above.

The amount of the superabsorbent material in the absorbent composite is about 50 weight percent or greater, preferably about 60 weight percent or greater, and more preferably about 70 or 80 weight percent or greater in order to minimize the amount of fluff pulp fibers which, as previously noted, have been found to be the major cause of plugging. The distribution of the superabsorbent material within the absorbent composite can be uniform or nonuniform, such as by being layered or otherwise nonuniformly placed within the absorbent composite.

For purposes herein, the term "superabsorbent material" is any material which is capable of absorbing or gelling at least 10 times its weight, preferably 15 times its weight, of body exudate or a suitable aqueous solution such as 0.9 weight percent solution of sodium chloride in distilled water. Such materials include, but are not limited to, hydrogel-forming polymers which are alkali metal salts of: poly(acrylic acid); poly(methacrylic acid); copolymers of acrylic and methacrylic acid with acrylamide, vinyl alcohol, acrylic esters, vinyl pyrrolidone, vinyl sulfonic acids, vinyl acetate, vinyl morpholinone and vinyl ethers; hydrolyzed acrylonitrile grafted starch; acrylic acid grafted starch; maleic anhydride copolymers with ethylene, isobutylene, styrene, and vinyl ethers; polysaccharides such as carboxymethyl starch, carboxymethyl cellulose, methyl cellulose, and hydroxypropyl cellulose; poly(acrylamides); poly(vinyl pyrrolidone); poly(vinyl morpholinone);

poly(vinyl pyridine); and copolymers and mixtures of any of the above and the like. The hydrogel-forming polymers are preferably lightly crosslinked to render them substantially water-insoluble. Crosslinking may be achieved by irradiation or by covalent, ionic, van der Waals attractions, or hydrogen bonding interactions, for example. A preferable superabsorbent material is a lightly crosslinked hydrocolloid. The superabsorbent materials can be in any form suitable for use in absorbent structures or composites, including particles, fibers, bicomponent fibers, filaments, flakes, spheres, and the like.

The fluff pulp fibers useful for the absorbent composite of this invention are preferably in the form of an airlaid batt of comminuted wood pulp (fluff), the formation and use of which is well known and established in the art of diaper manufacture. Although comminuted wood pulp is preferred, other cellulosic fibers, such as cotton linters, can also be used. Suitable synthetic fibers include, without limitation, fibers of polyethylene, polypropylene, polyesters, copolymers of polyesters and polyamides, bicomponent fibers, and the like. Mixtures of natural and synthetic fibers can also be used. The fibers used to form the matrix of the absorbent composite are generally hydrophilic or rendered hydrophilic through a suitable surface treatment. The preferred wood pulp fluff is produced by fiberizing bleached northern or southern softwood kraft pulp, although hardwood pulps and blends of hardwood and softwood pulps can also be used. By way of illustration, a blend of hardwood and softwood pulps can have a weight ratio of softwood pulp to hardwood pulp of from about 1:3 to about 20:1.

The absorbent composite of this invention comprises a porous matrix of fibers and superabsorbent material dispersed among the interfiber spaces and/or fiber pores. While particulate superabsorbent material is preferred because of its commercial availability, the superabsorbent material can also be in the form of continuous or discontinuous fibers. The formation of the absorbent composite can be accomplished in any number of ways, such as are currently used in the manufacture of commercially available diapers. A suitable example of one means of forming the absorbent composite is disclosed in U.S. Pat. No. 4,927,582 to Bryson et al.

Because the superabsorbent material in the absorbent composite is present in relatively high proportions, the absorbent composite of the present invention can be relatively thin while still functioning in an acceptable manner. Advantageously, the absorbent composites of this invention can have an average thickness of less than about 0.2 inch and preferably less than about 0.1 inch. As used herein, the average thickness is the average of a statistically significant number of thickness measurements taken under an applied load of 0.2 pounds per square inch. The number of thickness measurements taken depends on the size and uniformity of the absorbent composite, and must be sufficient to represent the average thickness of the entire absorbent composite.

DETAILED DESCRIPTION OF THE DRAWING

Figure 1:
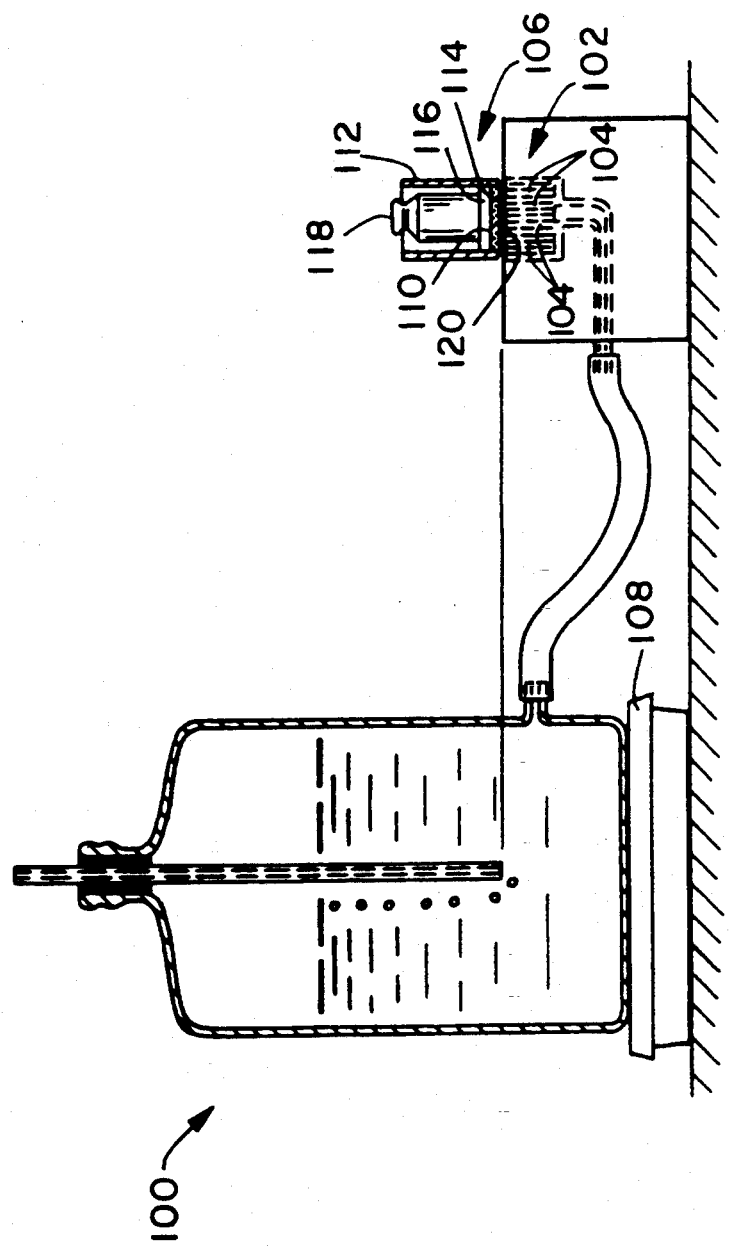
FIG. 1 is a cross-sectional view of the apparatus used to measure the Absorbency Under Load (AUL) of a superabsorbent material.

The Absorbency Under Load (AUL) test is a measure of the ability of a superabsorbent material to absorb a liquid while the superabsorbent material is under a restraining load. The test can best be understood by reference to FIG. 1, which is a cross-sectional view of the equipment used to measure the AUL of a superabsorbent material. Referring to FIG. 1, a demand absorbency tester (DAT) 100 is used, which is similar to a GATS (gravimetric absorbency test system), available from M/K Systems, Danners, Mass., as well as a system described by Lichstein in pages 129-142 of the INDA Technological Symposium Proceedings, March 1974. A porous plate 102 is used having ports 104 confined within the 2.5 centimeter area covered, in use, by the Absorbency Under Load apparatus 106. An electrobalance 108 is used to measure the flow of the test fluid (an aqueous solution containing 0.9 weight percent sodium chloride) into the superabsorbent material 110. The AUL apparatus 106 used to contain the superabsorbent material is made from 1 inch (2.54 centimeter), inside diameter, thermoplastic tubing 112 machined-out slightly to be sure of concentricity. One hundred mesh stainless steel wire cloth 114 is adhesively attached to the bottom of tubing 112. Alternatively, the steel wire cloth 114 can be heated in a flame until red hot, after which the tubing 112 is held onto the cloth until cooled. Care must be taken to maintain a flat, smooth bottom and not distort the inside of the tubing 112. A 4.4 gram piston 116 is made from 1 inch solid material (e.g., plexiglass) and is machined to closely fit, without binding, in the tubing 112. A 200 gram weight 118 (outer diameter 0.98) inch is used to provide 39,500 dynes per square centimeter (about 0.57 psi) restraining load on the superabsorbent material. A sample corresponding to a layer of at least about 300 grams per square meter (0.16 grams) of superabsorbent material is utilized for testing the Absorbency Under Load. The sample is taken from superabsorbent material which is prescreened through U.S. standard #30 mesh and retained on U.S. standard #50 mesh. The superabsorbent material, therefore, has a particle size of between 300 and 600 microns. The particles can be prescreened by hand or automatically with, for example, a Ro-Tap Mechanical Sieve Shaker Model B available from W. S. Tyler, Inc., Mentor, Ohio.

The test is initiated by placing a 3 centimeter diameter GF/A glass filter paper 120 onto the plate 102 (the paper is sized to be larger than the internal diameter and smaller than the outside diameter of the tubing 112) to ensure good contact while eliminating evaporation over the ports 104 of the demand absorbency tester 100 and then allowing saturation to occur. The desired amount of superabsorbent material 110 (0.16 grams) is weighed onto weigh paper and placed on the wire cloth 114 at the bottom of the tubing 112. The tubing 112 is shaken to level the superabsorbent material on the wire cloth 114. Care is taken to be sure no superabsorbent material is clinging to the wall of the tubing 112. After carefully placing the piston 116 and weight 118 on the superabsorbent material to be tested, the apparatus 106 is placed on the glass filter paper 120. The amount of fluid picked up is monitored as a function of time either directly by hand, with a strip chart recorder, or directly into a data acquisition or personal computer system.

The amount of fluid pick-up measured after 90 minutes is the AUL value and is reported in grams of test liquid absorbed per gram of superabsorbent material as determined before starting the test procedure. A check can be made to ensure the accuracy of the test. The apparatus 106 can be weighed before and after the test with a difference in weight equaling the fluid pick-up.

As used herein, the Centrifugal Retention Capacity (CRC) is a measure of the absorbent capacity of the superabsorbent material retained after being subjected to centrifugation under controlled conditions. The superabsorbent sample to be tested is taken from superabsorbent material which is prescreened through U.S. standard #30 mesh and retained on U.S. standard #50 mesh. The superabsorbent material therefore has a particle size of between 300 and 600 microns. The particles can be prescreened by hand or automatically as described above for the AUL. The CRC can be measured by placing 0.200 grams of the sample material to be tested (moisture content of less than 5 weight percent) into a water-permeable bag which will contain the sample while allowing the test solution (0.9 percent NaCl solution) to be freely absorbed by the sample. A heat-sealable tea bag material (grade 542, commercially available from Kimberly-Clark Corporation, Neenah, Wisc.) works well for most applications. The bag is formed by folding a 5 inches by 3 inches sample of the bag material in half and heat sealing two of the open edges to form a 2.5×3 inch rectangular pouch. The heat seals should be about 0.25 inch inside the edge of the material. After the sample is placed in the pouch, the remaining open edge of the pouch is also heat-sealed. Empty bags are also made to be tested with the sample bags as controls. Three sample bags are tested for each superabsorbent material.

The sealed bags are placed between two Teflon® coated fiberglass screens having ¼ inch openings (Taconic Plastics, Inc., Petersburg, N.Y.) and submerged in a pan of 0.9 percent NaCl solution at 73.4°+2° F., making sure that the screens are held down until the bags are completely wetted. After wetting, the samples remain in the solution for 30 minutes, at which time they are removed from the solution and temporarily laid on a nonabsorbent flat surface. The wet bags are then placed into the basket of a suitable centrifuge capable of subjecting the samples to a g-force of 350. (A suitable centrifuge is a Clay Adams Dynac II, model #0103, having a water collection basket, digital rpm gauge, and machined drainage basket adapted to hold and drain the flat bag samples). The samples must be placed in opposing positions within the centrifuge to balance the basket when spinning. The bags are centrifuged at a target of 1600 rpm, but within the range of 1500–1900 rpm, for 3 minutes (target g-force of 350). The bags are removed and weighed, with the empty bags (controls) being weighed first, followed by the bags containing superabsorbent material. The amount of fluid absorbed and retained by the superabsorbent material, taking into account the fluid retained by the bag material alone, is the Centrifugal Retention Capacity of the superabsorbent material, expressed as grams of fluid per gram of superabsorbent material.

The "30 Second Absorbent Capacity" is a measure of the amount of tap water a superabsorbent can gel in 30 seconds. It is measured by evenly spreading 0.025 grams of superabsorbent over the bottom of an AUL cylinder (previously described). The sample is taken from superabsorbent material which is sieved to a particle size of 300 to 600 microns. The cylinder is then submerged in a 100 ml beaker of test fluid to a depth sufficient to completely cover the superabsorbent particles. After 30 seconds of submersion, the cylinder containing the swollen sample is quickly removed from the test fluid and any excess fluid held in the interstices of the superabsorbent particles is removed by placing the wire mesh end of the cylinder on a piece of disposable paper toweling effectively blotting the superabsorbent. The cylinder and swollen superabsorbent are then weighed to determine the amount of fluid absorbed. The 30 Second Absorbent Capacity is expressed in grams of test fluid absorbed per gram of superabsorbent material as determined before starting the test.

For consistency, a standard tap water formulation has been developed. The standard fluid consists of 72 mg/l $CaCl_2$, 44 mg/l $NaHCO_3$, and 67 mg/l $MgSO_4$ 7 $H_2O$ all dissolved in distilled water. When making up the standard tap water care must be taken to add the $CaCl_2$ and the $NaHCO_3$ to a large enough quantity of distilled water to prevent precipitation of $CaCO_3$.

EXAMPLES

In order to illustrate the flushability of the absorbent composites of this invention, a number of experiments were conducted to quantify and compare the plugging propensity of several different materials. All of the superabsorbent materials tested were experimental materials from Dow Chemical except for IM5000P, which is a commercially available superabsorbent sold by Hoechst Celanese. The Dow materials are identified by lot number. Generally, the superabsorbent particles were combined with fluff pulp fibers to form an absorbent composite and wrapped in a containment material (rayon bonded carded web) and sealed with two-sided tape to form an absorbent pad similar in size and shape as would be expected to be used in an actual diaper. Unless otherwise stated, each pad weighed 20 grams and had dimensions of 13 inches long and 3.5 inches wide.

The absorbent pad samples were prewet with a 0.9 weight percent saline solution prior to flushing to simulate actual use. A cradle was used to support the pads during the prewetting process, in which each pad was folded into a "U" shape and positioned symmetrically so that the midsection of the pad was at the bottom of the cradle. 100 grams of the saline solution, which is the average urine load in diapers, was poured onto the midsection of the pad. At least 5 minutes of equilibration time was allowed before flushing.

The toilet used for the flushing tests was a Kohler® Wellworth™ Lite™ (K-3421). In some cases the toilet was modified by replacing the side of the trapway with a piece of clear plastic so the material could be observed passing through the trapway. The net effect on the functioning of the toilet was to make it less efficient in passing materials because the trapway became slightly narrower, less slippery, and several screw heads that held the plastic in place were slight snag hazards.

Each absorbent pad sample was lifted from the cradle and carefully folded either in half lengthwise (single-folded) or folded into thirds (double-folded) into a "Z" configuration. The folded pad was then placed in the toilet bowl so that the long dimension of the folded pad was either perpendicular or parallel to the long axis of the oblong toilet bowl. The absorbent pad was allowed to sit in the toilet bowl for 30 seconds before the toilet was flushed. If the sample failed to completely exit the entire fixture in one flush, it was deemed a plug.

EXAMPLE 1

Absorbent pads containing 80 weight percent superabsorbent and 20 weight percent fluff pulp were single-folded as described above and placed into the toilet bowl perpendicular to the axis of the toilet bowl and flushed. Fifty pads of each superabsorbent sample were flushed. The results are set forth in Table 1.

TABLE 1

| Superabsorbent | Percent Plugs |
|---|---|
| Dow 5-33 | 0 |
| Dow 5-15 | 0 |
| IM5000P | 18 |

EXAMPLE 2

The same flushability test was conducted as in Example 1, except the superabsorbent pad samples were double-folded. The results are set forth in Table 2.

TABLE 2

| Superabsorbent | Percent Plugs |
|---|---|
| Dow 5-33 | 14 |
| Dow 5-15 | 8 |
| IM5000P | 58 |

EXAMPLE 3

The same flushability test was conducted as described in Example 1, except the amount of superabsorbent in each of the pads was 60 percent. Fifty pads of the Dow 5-15 superabsorbent were tested. Twenty-five pads of the IM5000P superabsorbent were tested. The results are set forth in Table 3.

TABLE 3

| Superabsorbent | Percent Plugs |
|---|---|
| Dow 5-15 | 38 |
| IM5000P | 100 |

EXAMPLE 4

In this example, absorbent pads containing 80 weight percent superabsorbent and 20 percent pulp fluff were prepared as in Example 1, except two absorbent composites (34 grams total) were wrapped inside one containment wrap (rayon bonded carded web) to form a pad having a length of 12 inches and a width of 4.5 inches. The "double" pad was used to obtain a significant number of plugs with relatively few samples. The samples were not prewet. The toilet used was an unmodified Kohler Wellworth Lite (K-3421). The double absorbent pad samples were folded in half lengthwise and placed in the toilet so the long dimension of the sample was parallel to the major axis of the toilet bowl. The samples were allowed to sit in the toilet for 15 seconds before flushing. Twenty samples of the Dow 5-15 and Dow 5-31 materials were flushed and ten samples of the IM5000P material were flushed. The results are set forth in Table 4.

TABLE 4

| Superabsorbent | Percent Plugs |
|---|---|
| Dow 5-15 | 15 |
| Dow 5-31 | 95 |
| IM5000P | 100 |

EXAMPLE 5

Testing was conducted as described in Example 4, except the samples were placed in the toilet bowl so the long axis of the sample was perpendicular to the major axis of the toilet bowl. The number of samples for each superabsorbent material was the same. The results are set forth in Table 5.

TABLE 5

| Superabsorbent | Percent Plugs |
|---|---|
| Dow 5-15 | 70 |
| Dow 5-31 | 70 |
| IM5000P | 100 |

EXAMPLE 6

The purpose of this example was to determine how much absorbent composite material could be flushed before a plug occurred. Absorbent composite materials were 80 weight percent superabsorbent and 20 weight percent wood pulp fluff. Samples were not wrapped in a containment wrap and the samples were not prewet. A specific weight of dry absorbent composite material was randomly placed within the volume of toilet bowl water in the unmodified Kohler Wellworth Lite toilet. The material was allowed to sit for 30 seconds and then the toilet was flushed. If the material failed to exit the fixture in one flush it was recorded as a plug. This procedure was repeated with increasing amounts of superabsorbent composite material (ten samples per weight) until the approximate dry weight (in grams) of the absorbent composite material that would just barely plug (failure) was determined. The results are set forth in Table 6.

TABLE 6

| Superabsorbent | Amount at Failure (grams) |
|---|---|
| Dow 5-15 | 50 |
| Dow 5-31 | 40 |
| IM5000P | 38 |

EXAMPLE 7

Disposable diapers having a removable absorbent pad were made using an absorbent composite containing 80 weight percent superabsorbent material and 20 weight percent wood pulp fluff. The absorbent pads weighed 17 grams and were wrapped inside a rayon bonded carded web containment material. Fifty test subjects used and flushed the test products in their homes over a three day period. The users recorded any plugs that occurred. The sample size was approximately 600 diapers per superabsorbent material. The results are set forth in Table 7.

TABLE 7

| Superabsorbent | Percent Plugs |
|---|---|
| Dow 5-15 | 0.6 |
| IM5000P | 3.2 |

The properties of the various superabsorbents tested and their subjective flushability rating based on the foregoing results are set forth in Table 8 below.

TABLE 8

| Superabsorbent | AUL:CRC Ratio | 30 Sec. Abs. Cap. | Flushability |
|---|---|---|---|
| Dow 5-33 | 1.10 | 6 | Good |
| Dow 5-15 | 0.86 | 12 | Good |
| Dow 5-31 | 0.60 | 12 | Moderate |
| IM5000P | 0.33 | 32 | Poor |

The foregoing results illustrate that absorbent composites containing mixtures of superabsorbents and fluff pulp have good flushability if the superabsorbent material has an AUL:CRC ratio of greater than 0.60, and preferably also has a 30 second absorbent capacity of about 12 or less.

It will be appreciated that the foregoing examples, given for purposes of illustration, are not to be construed as limiting the scope of the invention, which is defined by the following claims and all equivalents thereto.

We claim:

1. A flushable absorbent composite comprising a matrix of fluff pulp fibers and superabsorbent particles wherein the superabsorbent particles have a ratio of the Absorbency Under Load to the Centrifuge Retention Capacity of about 1.10 or greater and a total absorbent capacity of at least 15 times their weight of a 0.9 weight percent solution of sodium chloride in distilled water.

2. The absorbent composite of claim 1 having about 50 dry weight percent or greater superabsorbent particles based on the combined weight of the superabsorbent particles and the fibers.

3. The absorbent composite of claim 2 wherein the amount of superabsorbent particles is about 70 dry weight percent or greater.

4. The absorbent composite of claim 2 wherein the amount of superabsorbent particles is about 80 dry weight percent or greater.

5. The absorbent composite of claim 1 wherein the amount of superabsorbent particles is about 80 weight percent or greater.

6. The absorbent composite of claim 1 having a 30 Second Absorbent Capacity of about 12 or less.

7. The absorbent composite of claim 1 having a 30 Second Absorbent Capacity of about 6 or less.

8. The absorbent composite of claim 1 wherein the superabsorbent particles comprise a covalently cross-linked hydrocolloid.

9. The absorbent composite of claim 1 wherein the superabsorbent particles are an alkali metal salt of a material selected from the group consisting of poly (acrylic acid), poly (methacrylic acid), copolymers of acrylic acid and methacrylic acid, hydrolyzed acrylonitrile grafted starch, acrylic acid grafted starch, and maleic anhydride copolymers with ethylene and poly (acrylamides).

10. A disposable diaper having a removable flushable absorbent pad containing an absorbent composite comprising a matrix of fluff fibers and about 80 dry weight percent superabsorbent particles based on the combined weight of the superabsorbent particles and the fibers, wherein the superabsorbent particles have a ratio of the Absorbency Under Load to the Centrifuge Retention Capacity of about 1.10 or greater, a 30 Second Absorbent Capacity of about 12 or less and a total absorbent capacity of at least 15 times their weight of a 0.9 weight percent solution of sodium chloride in distilled water.

11. The disposable diaper of claim 10 wherein the superabsorbent particles comprise a covalently cross-linked hydrocolloid.

12. The disposable diaper of claim 10 wherein the superabsorbent particles are an alkali metal salt of a material selected from the group consisting of poly (acrylic acid), poly (methacrylic acid), copolymers of acrylic acid and methacrylic acid, hydrolyzed acrylonitrile grafted starch, acrylic acid grafted starch, acrylic acid grafted starch, and maleic anhydride copolymers with ethylene and poly (acrylamides).

13. A flushable absorbent composite comprising a matrix of fluff pulp fibers and about 80 dry weight percent superabsorbent particles or greater based on the combined weight of the superabsorbent particles and the fibers, wherein the superabsorbent particles have a ratio of the Absorbency Under Load to the Centrifuge Retention Capacity of about 1.10 or greater, a 30 second Absorbent Capacity of about 12 or less and a total absorbent capacity of at least 15 times their weight of a 0.9 weight percent solution of sodium chloride distilled water.

14. The absorbent composite of claim 13 wherein the superabsorbent particles comprise a covalently cross-linked hydrocolloid.

15. The absorbent composite of claim 13 wherein the superabsorbent particles are an alkali metal salt of a material selected from the group consisting of poly (acrylic acid), poly (methacrylic acid), copolymers of acrylic acid and methacrylic acid, hydrolyzed acrylonitrile grafted starch, acrylic acid grafted starch, and maleic anhydride copolymers with ethylene and poly (acrylamides).

16. A disposable diaper having a removable flushable absorbent pad containing an absorbent composite comprising a matrix of fluff pulp fibers and superabsorbent particles wherein the superabsorbent particles have a ratio of the Absorbency Under Load to the Centrifuge Retention Capacity of about 1.10 or greater and a total absorbent capacity of at least 15 times their weight of a 0.9 weight percent solution of sodium chloride in distilled water.

17. The diaper of 16 wherein the amount of superabsorbent particles is about 50 dry weight percent or greater, based on the combined weight of the superabsorbent particles and the fibers.

18. The diaper of claim 17 wherein the amount of superabsorbent particles is about 70 dry weight percent or greater.

19. The diaper of claim 17 wherein the amount of superabsorbent particles is about 80 dry weight percent or greater.

20. The diaper of claim 16 wherein the absorbent composite has a 30 Second Absorbent Capacity of about 12 or less.

21. The disposable diaper of claim 16 wherein the superabsorbent particles comprise a covalently cross-linked hydrocolloid.

22. The disposable diaper of claim 16 wherein the superabsorbent particles are an alkali metal salt of a material selected from the group consisting of poly (acrylic acid), poly (methacrylic acid), copolymers of acrylic acid and methacrylic acid, hydrolyzed acrylonitrile grafted starch, acrylic acid grafted starch, and maleic anhydride copolymers with ethylene and poly (acrylamides).

* * * * *